United States Patent
Barnes et al.

(10) Patent No.: US 11,439,369 B1
(45) Date of Patent: Sep. 13, 2022

(54) METHOD AND APPARATUS FOR IMAGING WITH REDUCED LEVEL OF OFF-AXIS ARTIFACTS

(71) Applicant: Government of the United States, as represented by the Secretary of the Air Force, Wright-Patterson AFB, OH (US)

(72) Inventors: Ronald A. Barnes, San Antonio, TX (US); Hope T. Beier, San Antonio, TX (US); Bennett L. Ibey, San Antonio, TX (US); Caleb Roth, San Antonio, TX (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 479 days.

(21) Appl. No.: 15/794,358

(22) Filed: Oct. 26, 2017

(51) Int. Cl.
*A61B 8/08* (2006.01)
*A61B 8/00* (2006.01)

(52) U.S. Cl.
CPC .......... *A61B 8/5223* (2013.01); *A61B 8/5269* (2013.01); *A61B 8/54* (2013.01)

(58) Field of Classification Search
CPC ........ A61B 8/5223; A61B 8/5269; A61B 8/54
See application file for complete search history.

(56) References Cited

U.S. PATENT DOCUMENTS

| 3,790,252 | A | 2/1974 | Pao |
| 3,799,652 | A | 3/1974 | Torguet |
| 4,468,136 | A | 8/1984 | Murphy et al. |
| 5,517,349 | A | 5/1996 | Sandstrom |
| 6,041,020 | A | 3/2000 | Caron et al. |
| 6,754,000 | B2 | 6/2004 | Engelhardt et al. |
| 7,338,448 | B2 | 3/2008 | Hao et al. |
| 7,466,466 | B2 | 12/2008 | Ehrmann et al. |
| 8,137,272 | B2 | 3/2012 | Cooley et al. |
| 8,711,342 | B2 | 4/2014 | Elliott et al. |

(Continued)

OTHER PUBLICATIONS

Zhang, "Comparison of the Imaging Resolutions of Time Reversal and Back-Projection Algorithms in EM Inverse Scattering", 2013 (Year: 2013).*

(Continued)

*Primary Examiner* — Amanda Lauritzen Moher
*Assistant Examiner* — Brooke Lyn Klein
(74) *Attorney, Agent, or Firm* — AFMCLO/JAZ; Chastity D. S. Whitaker

(57) ABSTRACT

An acoustic imaging system responsive to an acoustic wave emitted from an object is disclosed. The system detects a deflection angle of an electromagnetic probe beam as it passes through a coupling element. The coupling element also couples the acoustic wave emitted from the object to an acoustic detector. The probe beam deflection angle is related to an angle of propagation of the acoustic wave through the coupling element. A filtering unit is configured to remove components of the signal from the acoustic detector that are outside of a range of angles, thereby improving the angular resolution of the acoustic detector. The acoustic wave may be generated by an acoustic source, such as an ultrasound transmitter, or an electromagnetic source such as a laser.

6 Claims, 7 Drawing Sheets

(56) References Cited

U.S. PATENT DOCUMENTS

| | | | |
|---|---|---|---|
| 9,535,309 B2 | 1/2017 | Rozsa et al. | |
| 2011/0184292 A1 | 7/2011 | Yoo et al. | |
| 2012/0157850 A1 | 6/2012 | Sumi et al. | |
| 2013/0041247 A1 | 2/2013 | Maswadi | |
| 2014/0378811 A1* | 12/2014 | Nanaumi | G01N 21/1702 |
| | | | 600/407 |
| 2015/0011882 A1 | 1/2015 | Abe | |
| 2018/0085091 A1* | 3/2018 | Hayashi | A61B 8/4405 |
| 2019/0369220 A1* | 12/2019 | Vignon | A61B 8/5269 |

OTHER PUBLICATIONS

Harazi, "Time reversal of ultrasound in granular media", 2016 (Year: 2016).*

Maswadi et al., "All-optical optoacoustic microscopy based on probe beam deflection technique," Photoacoustics 4, pp. 91-101, Feb. 24, 2016.

M. Kuniyil et al., "Chapter 7: Handheld Probe-Based Dual Mode Ultrasound/Photoacoustics for Biomedical Imaging," In Frontiers in Biophotonics for Translational Medicine (M. Olivo and U.S. Dnish, Eds) Springer 2016 (39 pages total).

J. J. Niederhauser et al., "Combined ultrasound and optoacoustic system for real-time high-contrast vascular imaging in vivo," IEEE Trans. Med. Imag., vol. 24 (2005) 436-440.

J. Czuchnowski et al., "Photoacoustics: seeing with sound," Science in School, Summer (2019) (5 pages total).

* cited by examiner

METHOD AND APPARATUS FOR IMAGING WITH REDUCED LEVEL OF OFF-AXIS ARTIFACTS

STATEMENT OF GOVERNMENT INTEREST

The invention described herein may be manufactured, used, and licensed by or for the Government of the United States for all governmental purposes without the payment of any royalty.

FIELD OF THE INVENTION

The present disclosure relates generally to methods, systems, apparatuses, and devices for ultrasonic imaging.

BACKGROUND OF THE INVENTION

Ultrasound imagers detect sound that results from an impedance discontinuity in an object. If the direction of the sound and its propagation time are known, the position of the impedance discontinuity may be calculated. However, an ultrasound detector has an angular resolution of approximately 15°, and this produces an uncertainty on the angle of arrival of the sound.

In ultrasound imaging applications, it is assumed that all acoustic signals measured by the transmitter/receiver transducer have been reflected back to the transducer at a 90° incident angle to the transducer aperture. In reality, when an ultrasound source encounters high-impedance boundaries, such as a gall bladder, cyst, stomach, etc., a large amount of energy is reflected off-axis, i.e., not at 90° to the transducer aperture. Traditional piezoelectric transducers are most responsive to sound propagating in a range of directions close to the axis of the sensor. This range of directions is sometimes referred to as the acceptance cone of the transducer. For example, a transducer may be most sensitive to sound propagating within 10° of the axis. As a result, some off-axis energy is measured by the transducer. If the angle of propagation of the sound is assumed to be along the axis, any off-axis sound is interpreted incorrectly and produces inaccuracies in the reconstructed image. The off-axis sound may result in an artifact in the image.

Accordingly, there exists a need to reduce artifacts in ultrasound images due to limited angular resolution of an ultrasound detector.

BRIEF SUMMARY OF THE INVENTION

The foregoing problems and other shortcomings, drawbacks, and challenges associated with artifacts in ultrasound imaging are overcome by the embodiments described herein. While the invention will be described in connection with certain embodiments, it is understood that it is not limited to these embodiments. To the contrary, the present invention includes all alternatives, modifications, and equivalents within the scope of the embodiments disclosed.

In accordance with embodiments described herein, an acoustic imaging system has a first electromagnetic source, a probe beam deflection detector, a coupling element that couples an acoustic wave emitted from an object to an acoustic detector and further couples a probe beam generated by the first electromagnetic source to the probe beam deflection detector, and a filtering unit, where the acoustic detector produces a first signal indicative of acoustic wave at the acoustic detector and the probe beam deflection detector produces a second signal indicative of a deflection of the probe beam. The filtering unit can determine, from the second signal, an angle of propagation of the acoustic wave through the coupling element and provide a filtered first signal by at least reducing the first signal in time intervals during which the angle of propagation is outside of a specified range of angles.

An acoustic imaging system having improved angular resolution is disclosed, with the detection system having an acoustic detector configured to produce a first signal indicative of an acoustic wave at the acoustic detector, where the acoustic detector is responsive to an acoustic wave propagating within a first range of angles; a first electromagnetic source configured to generate a first probe beam; a probe beam deflection detector configured to produce a second signal indicative of a deflection angle of the probe beam; a coupling element that couples an acoustic wave emitted from an object to the acoustic detector and further couples the first probe beam generated by the first electromagnetic source to the probe beam deflection detector; and a filtering unit. The filtering unit is configured to: determine, from the second signal, an angle of propagation of the acoustic wave through the coupling element; and provide a filtered first signal by at least reducing the first signal in time intervals during which the angle of propagation is outside of a second range of angles, where the second range of angles is smaller than the first range of angles.

In accordance with various disclosed embodiments, a method for imaging an object may include coupling an acoustic wave from the object through a coupling element to an ultrasonic detector to provide a first signal indicative of the acoustic wave at the ultrasonic detector; propagating an electromagnetic probe beam through the coupling element to a probe beam deflection detector to provide a second signal indicative of a deflection angle of probe beam; determining, from the second signal, an angle of propagation of the acoustic wave through the coupling element; and providing a filtered first signal by at least reducing the first signal in time intervals during which the angle of propagation is outside of a specified range of angles.

Additional objects, advantages, and novel features of the invention will be set forth in part in the description that follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings provide visual representations which will be used to more fully describe various representative embodiments. They can be used by those skilled in the art to better understand the representative embodiments disclosed and their inherent advantages. The drawings are not necessarily to scale, emphasis instead being placed upon illustrating the principles of the devices, systems, and methods described herein. In these drawings, like reference numerals may identify corresponding elements.

DETAILED DESCRIPTION OF THE INVENTION

Figure 1:
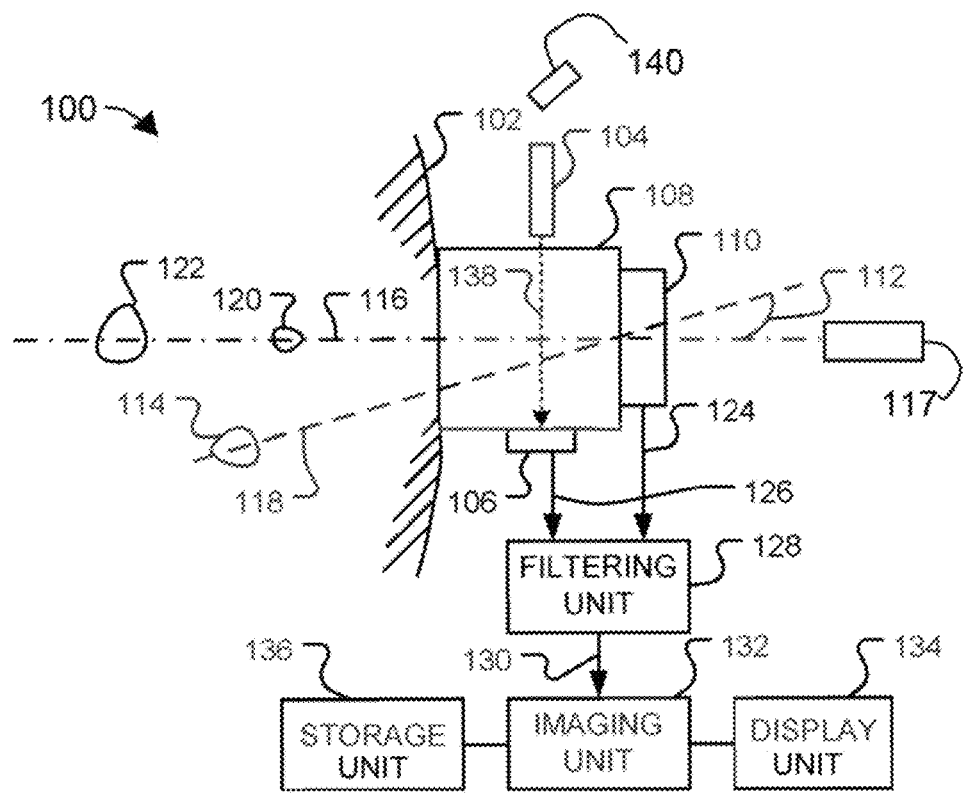
FIG. 1 is a block diagram of an ultrasound imaging system, consistent with embodiments of the disclosure.

The various methods, systems, apparatus, and devices described herein generally provide for improved ultrasonic imaging.

While this invention is susceptible of being embodied in many different forms, there is shown in the drawings and will herein be described in detail specific embodiments, with the understanding that the present disclosure is to be considered as an example of the principles of the invention and not intended to limit the invention to the specific embodiments shown and described. In the description below, like reference numerals may be used to describe the same, similar, or corresponding parts in the several views of the drawings.

Ultrasound imaging relies on an analysis of ultrasound emitted by an object. When an object is exposed to ultrasound, the ultrasound propagating in the object interacts with acoustic impedance variations within the object and returns to a transducer. By analyzing the ultrasound being emitted by this interaction and detected by the transducer, an image can be formed.

Traditional ultrasound and photoacoustic receivers utilize piezoelectric transducers that operate with electro-mechanic mechanisms. For example, in medical applications, phased array transducers with many elements (256 elements, for example) are utilized to image a soft tissue target. A transducer is most sensitive to sound propagating along its axis, but it also responds to sound within a range of incident angles, called the acceptance cone. An incident angle is defined as the angle between the axis of the transducer and the propagation direction of the ultrasound. For purposes of the present disclosure, it is assumed that the axis of the transducer is at 90° to the aperture of the transducer, but the axis may be at another angle. For example, in a phased array the axis may be varied.

Conventional ultrasound systems assume that ultrasound being detected at the transducer is received on-axis (i.e. incident at 0° to the axis of the transducer). In practice, some ultrasound received 'off-axis', that is, at an incident angle other than 0° to the axis of the transducer. If the resulting signal from the transducer is interpreted by the ultrasound system as being on-axis, an artifact (such as a false or misplaced impedance discontinuity) is created in the resulting ultrasound image, and therefore the quality of the image is decreased. For example, a system that uses a time-reversal back-projection approach produces an image of the received energy utilizing the speed of sound in the media and the time of arrival to resolve distance, but assumes that the sound is received on-axis.

One embodiment of the present disclosure relates to a technique for determining when ultrasound is received on-axis rather than off-axis. An image may then be constructed from the on-axis sound only, resulting in a reduction in artifacts in the image.

The approach makes use of a coupling element containing a medium having a refractive index that supports and is responsive to the propagation of both acoustic waves and electromagnetic waves. An acoustic wave in an object is coupled to an acoustic detector via the coupling element. The acoustic wave alternately compresses and expands the medium through which it travels. In an optically transparent medium, for example, this compression and expansion of the medium causes dynamic changes in the refraction index of the medium. When electromagnetic waves propagate through a medium, they interact with refractive index variations caused by propagation of the acoustic waves. Thus, as acoustic waves propagate through the coupling element, they can alter the propagation of an electromagnetic wave in the same medium.

Deflection of an electromagnetic beam, such as a laser beam, by sound waves in a medium has previously been used in other applications and is referred to a Probe Beam Deflection Technique (PBDT). For example, a controlled sound wave may be used to produce a controlled deflection in a laser beam. In a further application, the measured deflection of a laser beam has been used to sense an acoustic wave in a transparent medium.

In accordance with the present disclosure, when an electromagnetic beam is transmitted through the coupling element, its path will be altered by changes in the refractive index of the medium. The spatial gradient of the refractive index varies dynamically in the direction of propagation, so the probe beam is deflected in a plane that contains the direction of propagation and the direction of generation of the probe beam. This deflection can be measured by an appropriate sensor for detecting the electromagnetic beam, such as an optical sensor for a laser beam. Thus, the angle of deflection of the beam is an indicator of the direction of propagation of ultrasound in the coupling element. Ultrasound with a propagation angle outside of a specified range can be eliminated from construction of an image, thereby reducing the occurrence of artifacts in the resulting image. In this way, the appearance of off-axis artifacts in ultrasound and photoacoustic images is reduced by utilizing the angular information obtained from the PBDT.

Thus, embodiments of the present disclosure combine the PBDT with a traditional transducer to enable filtering of off-axis energy and reduce off-axis artifacts in acoustic and photoacoustic imaging. In other words, embodiments of the present disclosure provide the capability to resolve and quantify the angle of incidence for any received acoustic signal. For purposes of the present disclosure, illustrative embodiments will be described with reference to ultrasound, but the principles and teachings of these embodiments can be adapted to apply to any acoustic imaging system. By quantifying the angle of incidence of the acoustic waves being used in such systems, off-axis artifacts in the resulting image can be reduced.

FIG. 1 is an illustration of an ultrasound imaging system 100 consistent with embodiments of the present disclosure. Ultrasound imaging system 100 is responsive to ultrasound emitted from an object 102 to form an image of an interior of the object 102. The ultrasound imaging system 100 includes a first electromagnetic source 104, such as a laser, that generates a probe beam 138, and a probe beam deflection detector 106. Probe beam deflection detector 106 may include one or more sensors (not pictured) for detecting and/or sensing the probe beam, such as a quadrature photodiode, a bisectional diode, a knife-edge diode, or other detector for example. Alternatively, the probe beam deflection detector 106 may include a bisectional photodiode or knife-edge photodiode setup. In one embodiment, first the electromagnetic source 104 of the probe beam 138 is a laser diode that is transmitted through an optically transparent perfectly matched layer (PML) attached to the aperture of a traditional piston geometry medical ultrasound transducer. The laser diode can have any wavelength. For example, in certain embodiments the wavelength is in the range 380 nm-750 nm. A quadrature photodiode may be embedded at an opposite end of the PML and connected to differential amplifier electronics via cables. The quadrature photodiode is therefore configured to detect the propagation angle of any ultrasound reflection being measured by the piston transducer.

A coupling element 108 couples the ultrasound emitted from the object 102 to an ultrasound detector 110 and further couples the probe beam 138 from electromagnetic source 104 to the probe beam deflection detector 106.

Ultrasound emitted from object 102 may be caused by interaction of ultrasound with one of more acoustic impedance discontinuities 114, 120, 122 within the object 102. Ultrasound is propagated from the impedance discontinuity 114, 120, 122 to the ultrasound detector 110 at a propagation angle. For example, ultrasound from impedance discontinuity 114 propagates through coupling element 108 and is incident at an angle 112 with a transducer axis 116. The incident angle 112 denotes the angle between transducer axis 116 (which, in this example, is perpendicular to the aperture of the ultrasound detector 110) and direction of propagation 118. When the angle 112 is within the angle of acceptance of the transducer 117, the transducer 117 will respond to the ultrasound.

In the example shown, ultrasound from other impedance discontinuities 120, 122 is propagated along the direction 116 and has an incident angle of zero (that is, the ultrasound is incident along the axis of the ultrasound detector 110). On its own, the ultrasonic detector 110 cannot distinguish between sound received along the propagation path (i.e., the transducer axis 116) and that received along the propagation path i.e., the direction of propagation 118).

The ultrasound detector 110 produces a first signal, in a first signal path 124, indicative of the ultrasound received at the ultrasound detector 110, and the probe beam deflection detector 106 produces a second signal, in a second signal path 126, indicative of the deflection of probe beam incident angle 112 of the ultrasound through the coupling element 108. A filtering unit 128 determines, from the signals of the second signal path 126, the incident angle 112 of ultrasound relative to the transducer axis 116. Signal of the first signal path 124 is then filtered in a manner that is dependent upon the incident angle 112 to provide a filtered ultrasound signal 130. This method of filtering signal of the first signal path 124 based on the signal of the second signal path 126 removes (or at least reduces) the signal resulting from incident angles 112 that are outside of a selected range of angles. The signal of the second signal path 124 may be used to identify one or more time intervals during which the incident angle 112 is within this selected range of angles.

The selected range of angles can be established to reduce off-axis artifacts based on a variety of considerations, such as the acceptance cone of the transducer, its angular resolution, or the like, as well as considerations related to the area to be imaged. For example, the system 100 may use only ultrasound propagated within 1° of the transducer axis 116 to construct an image. In a further example, the system 100 may use only ultrasound propagated within 0.1° of the transducer axis 116 to construct an image. The range of angles may be selected dependent upon the angular resolution of the probe beam deflection detector 106. In turn, this resolution may be proportional to waist of the probe beam, which may be of the order of 0.1° in some embodiments. The waist of the probe beam is a measure of the beam size at the point of its focus, where the beam width is the smallest and the on-axis intensity is the largest. The imaging unit 132 receives the filtered ultrasound signal 130 and forms an image of the object 102 therefrom.

The image of the object may be formed from the signal of the first signal path 124 received in the one or more time intervals by determining an image pixel value from a strength of the signal and determining a first image pixel coordinate from an arrival time of the signal. The first coordinate denotes a depth of the impedance discontinuity 114, 120, 122 within the object 102. A second image pixel coordinate may be determined from a position of the ultrasound detector 110 as it is moved across a surface of the object 102.

The ultrasonic detector 110 may comprise an array of phased elements, which enables the transducer axis 116 to be steered by altering the relative phases of the elements in the array. An image of the object 102 is formed from the first signal received in the one or more time intervals by determining an image pixel value from a strength of the first signal, determining a first image pixel coordinate from an arrival time of the first signal, and determining a second image pixel coordinate from the steered direction of the array. The image of the object may be formed using a time-reversal, back-propagation technique, for example.

The image may be displayed on display unit 134 or saved in storage unit 136. The display unit 134 and storage 136 may be located in proximity to the imaging unit 132, integrated with the imaging unit 132, or coupled to the imaging unit 132 via a network, for example.

The ultrasound imaging system 100 may also include an ultrasound transmitter (not shown), where the ultrasound emitted from the object 102 is in response to ultrasound generated by the ultrasound transmitter and incident on the object 102. In some embodiments, for example, ultrasound detector 110 may also be used as an ultrasound transmitter. Alternatively, an ultrasound transmitter may be placed on the opposing side of object 102 from ultrasound detector 110.

In a further embodiment, a second electromagnetic source 802, such as a laser, may be used to generate ultrasound in the object 102. The second electromagnetic source 802 may function to cause a thermo-elastic effect by local heating of the surface of the object 102. This is discussed below with reference to FIG. 8.

During operation, ultrasound emitted from the object 102 propagates through coupling element 108 to ultrasonic detector 110 to provide a first signal, in signal path 124, indicative of ultrasound at the ultrasonic detector 110. At or about the same time, an electromagnetic probe beam 138 is passed through the coupling element 108 to probe beam deflection detector 106 to provide a second signal in signal path 126 indicative of the probe beam deflection. The second signal may be used to identify one or more time intervals during which the incident angle 112 is within a selected range of angles. The image of the object may be formed from the first signal received in the one or more time intervals by determining an image pixel value from a strength of the first signal, determining a first image pixel coordinate from an arrival time of the first signal. The first coordinate denotes the depth of the impedance discontinuity within the object. Second image pixel coordinates may be determined from a position of the ultrasound detector as it is moved across the surface of the object.

Ultrasonic detector 110 may comprise an array of phased elements, which enables the axis of the transducer to be steered by altering the relative phases of the elements in the array. An image of the object is formed from the first signal received in the one or more time intervals by determining an image pixel value from a strength of the first signal, determining a first image pixel coordinate from an arrival time of the first signal, and determining a second image pixel coordinate from the steered direction of the array. The image of the object may be formed using a time-reversal, back-propagation technique, for example.

In accordance with the embodiment shown in FIG. 1, ultrasound imaging system 100 is responsive to ultrasound emitted from object 102 and comprises a first electromagnetic source 104, probe beam deflection detector 106, coupling element 108 that couples ultrasound emitted from the object to an ultrasound detector 110 and further couples a probe beam 130 generated by the first electromagnetic source 104 to the probe beam deflection detector. The ultrasound detector 110 produces a first signal indicative of the ultrasound at the ultrasound detector. The probe beam deflection detector produces a second signal indicative of an incident angle 112 of the ultrasound through the coupling element. The ultrasound imaging system 100 also includes imaging unit 124 configured to determine, using the second signal, one or more time intervals during which the angle of propagation, through the coupling element, of ultrasound received at the ultrasound detector is within a first range of angles, and form an image of the object from the received first signal received in the one or more times intervals. For example, the system may use only ultrasound propagated within 1° of the transducer axis to reconstruct an image. In a further example, the system may use only ultrasound propagated within 0.1° of the transduce axis to reconstruct an image. The range of angles may be selected dependent upon the angular resolution of the probe beam deflection detector. In turn, this resolution may be proportional to waist of the probe beam, which may be of the order of 0.1° in some embodiments. The waist of the probe beam is a measure of the beam size at the point of its focus, where the beam width is the smallest and the on-axis intensity is the largest.

The ultrasound imaging system 100 may also have an ultrasound transmitter (not pictured), where the ultrasound emitted from the object is produced in response to ultrasound generated by the ultrasound transmitter and incident on the object.

The probe beam deflection detector may include one or more sensors for detecting and/or sensing the probe beam, such as a quadrature photodiode, a bisectional diode, a knife-edge diode or other detector.

Figure 2:
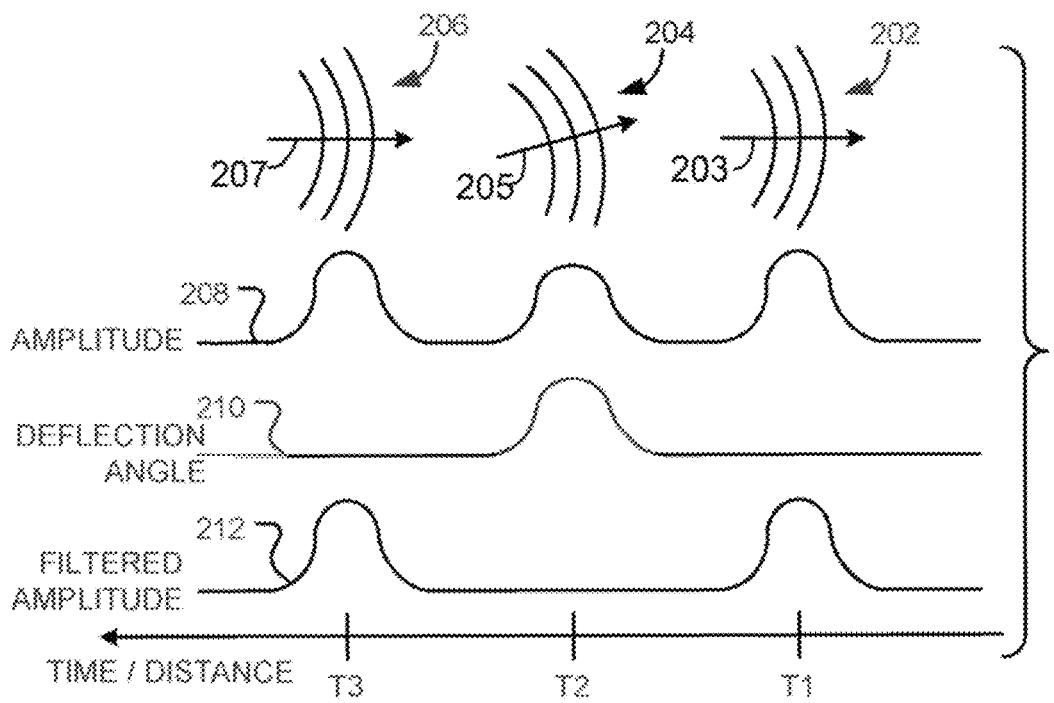
FIG. 2 is an illustration of signals in an ultrasound imaging system, consistent with embodiments of the disclosure.

Operation is summarized in FIG. 2, which shows three consecutive ultrasound pulses 202, 204, 206 emitted from the object 102 (FIG. 1). The ultrasound may be emitted, for example, in response to ultrasound wave from a transmitter being incident on the object. The pulse 202, received at the ultrasound detector 110 (FIG. 1) at a first time, T1, is due to the impedance discontinuity 120 (FIG. 1) at 0° to the transducer axis 116 of the ultrasound detector 110 (indicated by arrow 203). The second pulse 204, received at the ultrasound detector 110 (FIG. 1) at a second time, T2, is from the off-axis impedance discontinuity 114 (FIG. 1). The direction of propagation of the second pulse 204 (indicated by arrow 205) is not at 0° relative to the transducer axis 116 (FIG. 1) of the ultrasound detector 110 (FIG. 1). The third pulse 206, received at the ultrasound detector 110 (FIG. 1) at a third time, T3, is due to the impedance discontinuity 122 (FIG. 1) at 0° relative to the transducer axis 116 (FIG. 1) of the ultrasound detector 110 (FIG. 1) and is propagating in a direction indicated by arrow 207. The third pulse 206 arrives at a later time than the second pulse 202 because it is farther from the ultrasound detector 110 (FIG. 1). Thus, the time access in FIG. 2 is also a distance axis.

The three pulses 202, 204, 206 are received at the ultrasound detector 110 (FIG. 1) and produce signals in the first signal path 124 (FIG. 1) for generating an image. Amplitudes of these signals are shown in simplified form as graph 208. Each ultrasound pulse produces a corresponding amplitude pulse in the signal.

The probe beam deflection angle is detected to produce signal of the second signal path 126, which is shown as graph 210 in FIG. 2. The first ultrasound pulse 202 at time T1 causes little or no deflection in the graph 210 since the variation and refractive index caused by the ultrasound is symmetric in the coupling element 108 (FIG. 1) with respect to the propagation path of the probe beam (i.e., the transducer axis 116). The same is true for the third ultrasound pulse 206 at time T3. However, the second ultrasound pulse 204, and the resulting change in refractive index, is not symmetric with respect to the probe beam path. Consequently, this pulse 204 causes a deflection in the graph 210 at time T2, which will correspond to signal in the second signal path 126 (FIG. 1). In one embodiment, the times T1, T2, T3 are determined as the times at which the amplitude of the signal associated with each pulse 202, 204, 206 is at a maximum, as illustrated in graph 208. The corresponding values in the graph 210 (the beam defection signal) at the times T1, T2, T3 are used to determine if the signal of the first signal path 124 (FIG. 1) (i.e., graph 208) should be used in the construction of the image. In this example, the signal at time T2, associated with second pulse 204, indicates a propagation angle outside of a designated or specified range of angles. As a result, the signal associated with the second pulse 204 in the first signal path 124 (FIG. 1), in the time interval around time T2 is removed. This results in filtered signal 212 in FIG. 2. The range of angles may be determined dependent upon the angular resolution of the PBDT embodiment. For example, if the PBDT embodiment has an angular resolution of 0.1° then angles more than 0.1° off-axis in any direction would be filtered out.

If the signal associated with the second pulse 204 at time T2 was included in image reconstruction, an off-axis artifact would result. However, when the filtered signal 212 is used to construct the image there is no off-axis artifact in the image.

This technique may be used to provide an angular resolution of less than 1°, for example, by filtering out ultrasound that propagates at an angle more than 1° from the transducer axis 1156 of the ultrasound detector 110. The improved angular resolution compared with prior techniques provides a reduction or elimination of an off-axis artifact and improves ultrasound/photoacoustic image quality.

Figure 3:
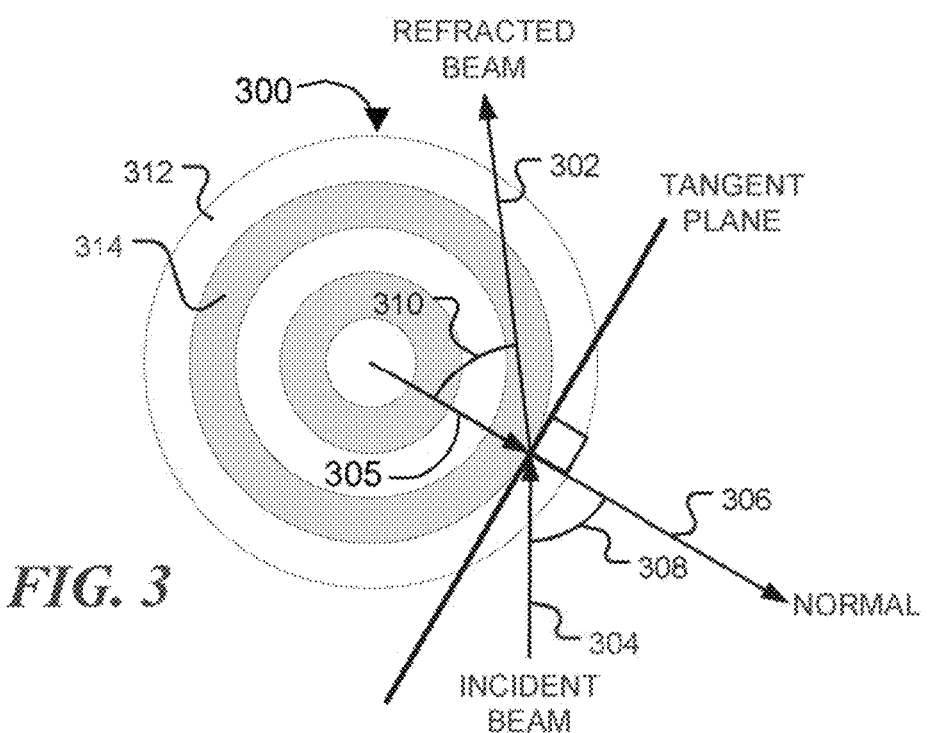
FIG. 3 illustrates the refraction of a probe beam as it passes through a region of varying refractive index due to an acoustic source, consistent with embodiments of the disclosure.

Referring now to FIGS. 1 and 3, an acoustic wave propagating wavefront 300 in the coupling element 108 may produce time-varying changes in the refractive index (adjacent regions 312, 134 having different refractive indices) of the coupling element 108. The varying refractive index causes refraction in the probe beam 304 as it passes to a boundary between regions 312, 314 region of varying refractive index. A tangential plane is defined by the point of interaction between the incident beam 304 and the propagating wavefront 300. A normalized plane vector 306 is shown and is the line that is normal to the tangential plane. A first angle 308 and a second angle 310, respectively, are the incidence and refraction angles at each side of the refractive index boundary (relative to the normalized plane vector). The subscript k identifies the region. While the first and second regions 312, 314 varying in refractive index are shown to be distinct in FIG. 3, the refractive index may be smoothly varying in practice.

The deflection of the probe beam 304 as it intersects with a boundary of the regions 312, 314 of refractive index gradients or boundaries is governed by Snell's law. In particular, a refracted beam 302, $v_{k+1}$, is given by:

$$v_{k+1} = \frac{n_k}{n_{k+1}} v_k + \left( \cos\theta_{k+1} - \text{sgn}(n_k \cdot v_k) \frac{n_k}{n_{k+1}} \cos\theta_k \right) n_k. \quad (1)$$

In equation (1), $\text{sgn}(n_k \cdot v_k)$ denotes the sign of the dot product between $n_k$ and $v_k$, the normalized plane vector 306 and the probe beam 304, respectively. The refracted beam 302 is directly correlated to the angle of incidence, $\theta_k$ (illustrated as angle 308) relative to the normalized plane vector 306. Therefore, the probe beam 304 deflects in a direction correlated to the propagation direction of the acoustic wave propagating wavefront 300. It is noted that the refractive indices $n_k$ and $n_{k+1}$ in the regions 312, 314 are dependent upon the strength of the ultrasound signal.

Figure 4A:
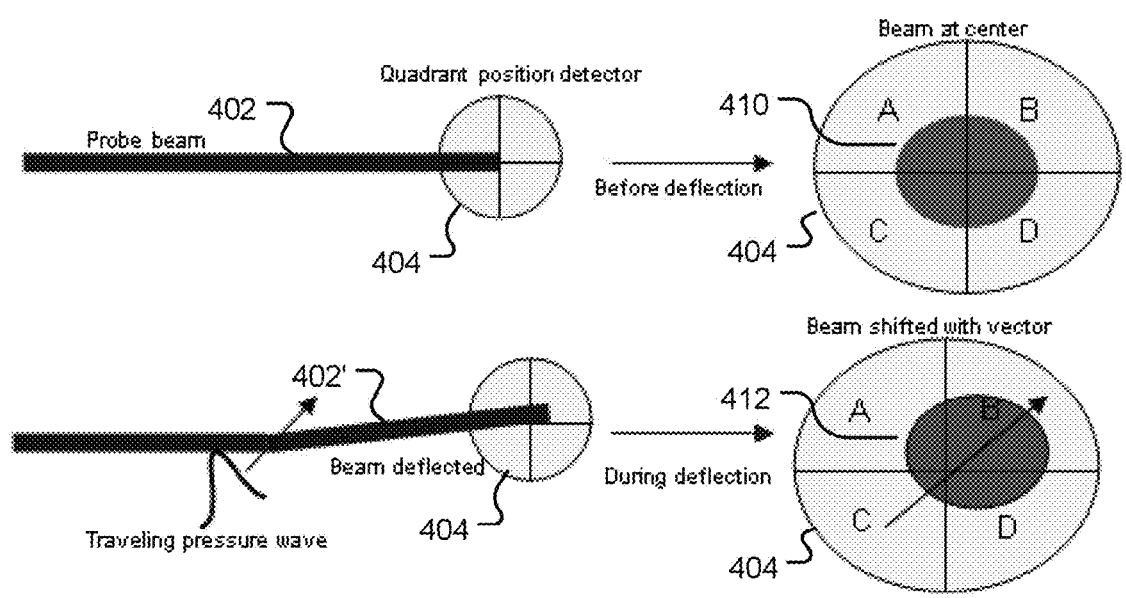
FIG. 4A is a diagram of probe beam/acoustic interaction and deflection detection with a quadrature photodiode, consistent with embodiments of the disclosure.
Figure 4B:
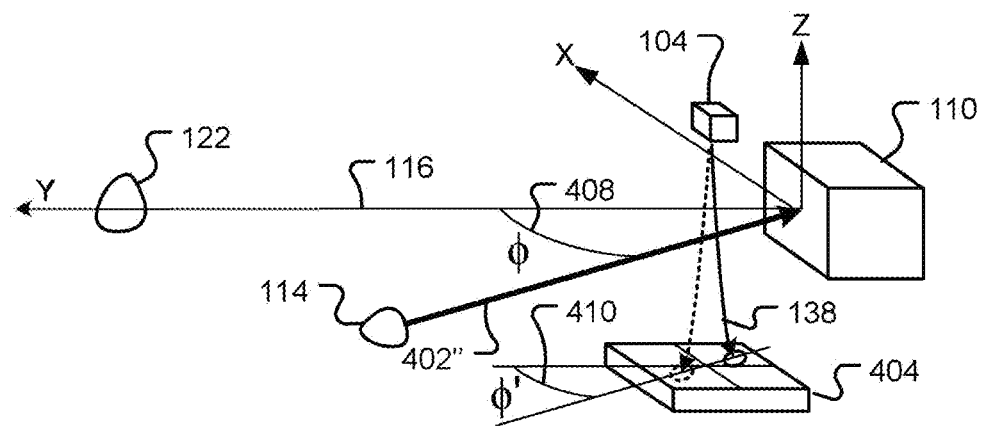
FIG. 4B is a diagram illustrating probe beam deflection by an acoustic wave in a coupling element, consistent with embodiments of the disclosure.

Referring now to FIGS. 1 and 4, the probe beam deflection detector 106 is configured to detect the deflection angle of the probe beam 138, which is related to the propagation angle of the ultrasound. For example, when the probe beam 138 is generated by a laser beam, the probe beam deflection detector 106 may include a quadrature photodiode. In such an embodiment, the movement of the beam across the face of quadrature photodiode can be translated into differential voltage signals that can represent the signal associated with an angle of propagation of the ultrasound that is routed to the second signal path 126. A diagram of probe beam/acoustic interaction and deflection detection with quadrature photodiode (the probe beam deflection detector 106) can be seen in FIG. 4A and FIG. 4B. The upper diagram in FIG. 4A shows probe beam 138 incident on a deflection detector 106 and resulting in a detected beam 410 that is centered. In this embodiment, the deflection detector 106, being a quadrature photodiode comprises four regions indicated as A, B, C and D. In the lower diagram of FIG. 4A, the probe beam 138 is deflected by an angle, θ, and the deflected beam 402 is sensed as a detected beam 412, which is offset by an angle, φ. The degree of offset may be determined via signals of the detected beams 410, 412 acquired from the quadrature photodiode (X,Y), where X and Y are spatial components of the probe beam deflection. Denoting a, b, c and d as the signals from detector regions A, B, C and D, respectively, the first (X) and second (Y) spatial components of the signal are given by:

$$X = \frac{(a+c)-(b+d)}{a+b+c+d}, \quad Y = \frac{(a+b)-(c+d)}{a+b+c+d}. \quad (2)$$

Referring now to FIG. 4B, the angle of incidence 112 is the angle between the transducer axis 116 and the direction of propagation 118. The beam deflection angle 410 in FIG. 4B is the angle around the un-deflected direction (probe beam 138) and is given by:

$$\tan\phi = \frac{Y}{X}. \quad (3)$$

Referring again to FIG. 4A, in the upper diagram, the probe beam excites the detected beam 410 of quadrature photodiode 106. The probe beam 138 is not deflected and so the detected beam 410 is centrally located. All four detector signals are equal and the result beam deflection angle, given by expression (3), is zero. In the lower diagram, the deflected beam 402 is deflected before hitting probe beam deflection detector 106 with the detected beam 412. The resulting detector signals a, b, c, and d are unequal, resulting in a non-zero beam deflection angle.

The configuration shown in FIG. 4A and FIG. 4B uses a vertically orientated probe beam 138 to detect deflection in a horizontal plane. A further probe beam oriented in a horizontal direction may be used to detect deflection in a vertical plane.

Figure 5A:
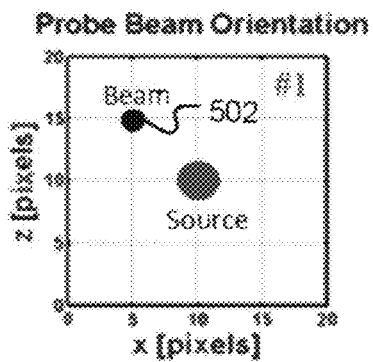
FIGS. 5A-5C and 6A-6C show experimental data illustrating the relationship between acoustic wave propagation direction and beam deflection angle, consistent with embodiments of the disclosure.
Figure 5B:
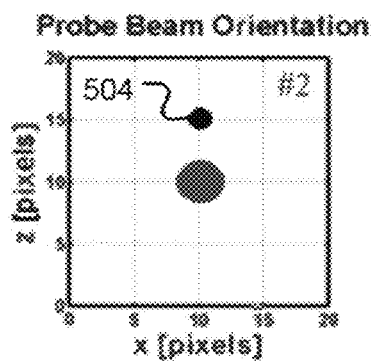
Figure 5C:
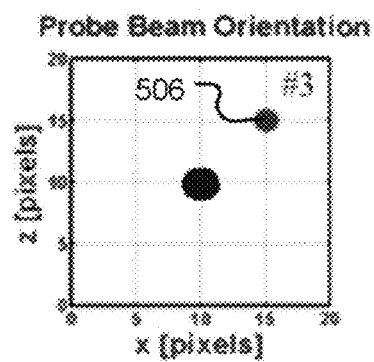
Figure 6A:
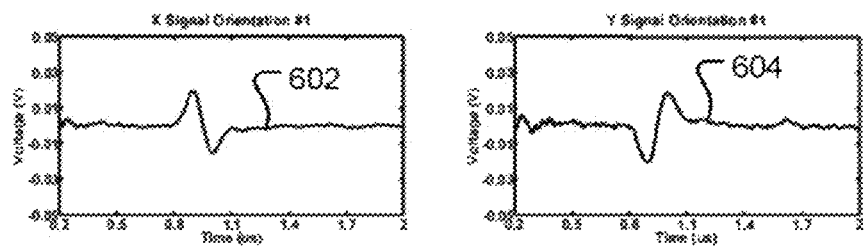
Figure 6B:
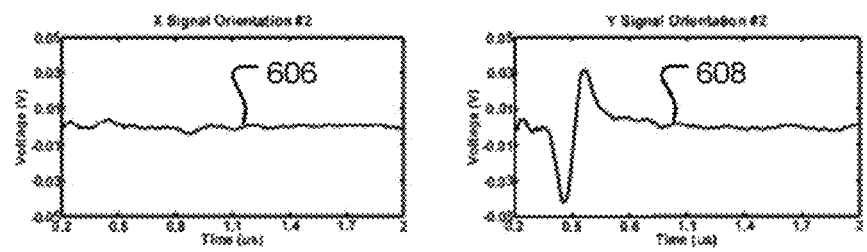
Figure 6C:
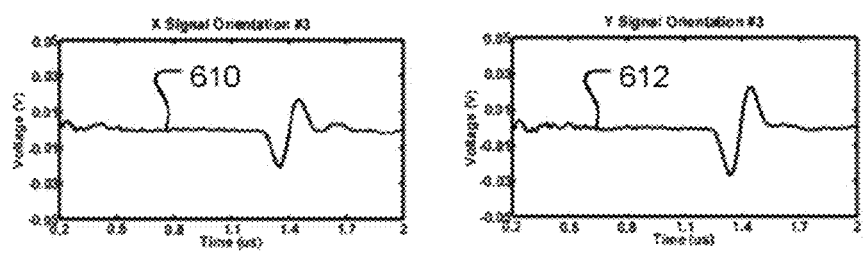

FIGS. 5A-5C and 6A-6C show experimental data demonstrating that a quadrature photodiode (acting as the probe beam deflection detector 106 of FIG. 1) may be used to indicate beam deflection. In the experiment, a laser probe beam was moved to three locations relative to a fixed acoustic source (indicated in the figures as "source") and the resulting quadrature photodiode signals were acquired. The quadrature photodiode was coupled to differential amplifiers resulting in two signals for each orientation. One signal (X) represents the motion of the detected beam along the horizontal axis, and the second signal (Y) represents the motion of the detected beam along the vertical axis. FIGS. 5A-5C show exemplary detected beams positions, 502, 504, 506, relative to the source as measured by a pixel array image sensor at particular times. A pixel array comprises an array of photodetectors. In a pixel array, the position of the beam is indicated by the location in the pixel array of the photodetector having the largest response. This may be used to verify equation (3) above. FIGS. 6A-6C show corresponding time histories of X and Y signals from a quadrature photodetector.

In FIG. 5A the detected beam 502 is deflected to the left and vertically. The corresponding X and Y signals are shown by graphs 602 and 604, respectively, in FIG. 6A. Graph 602 (X) shows maximum followed by a minimum indicating a shift to the left, while graph 604 (Y) shows a minimum followed by a maximum indicating a shift upwards.

In FIG. 5B the detected beam 504 is only deflected vertically. The corresponding X and Y signals are shown by graphs 606 and 608, respectively, in FIG. 6B. Graph 606 (X) shows no peaks, indicating no horizontal shift, while graph 608 (Y) shows minimum followed by a maximum indicating a shift upwards.

In FIG. 5C the detected beam 506 is deflected to the right and vertically. The corresponding X and Y signals are shown by graphs 610 and 612, respectively, in FIG. 6C. Graph 610 (X) shows minimum followed by a maximum indicating a shift to the right, while graph 612 (Y) shows minimum followed by a maximum indicating a shift upwards.

In one embodiment, the electromagnetic source of the probe beam is a laser diode that is transmitted through an optically transparent perfectly matched layer (PML) attached to the aperture of a traditional piston geometry medical ultrasound transducer. The laser diode can have any wavelength. For example, in certain embodiments the wavelength is in the range 380 nm-750 nm.

The quadrature photodiode may be embedded at the opposite end of the PML and connected to differential amplifier electronics via cables. The quadrature photodiode is therefore configured to detect the propagation angle of any ultrasound reflection being measured by the piston transducer.

Figure 7:
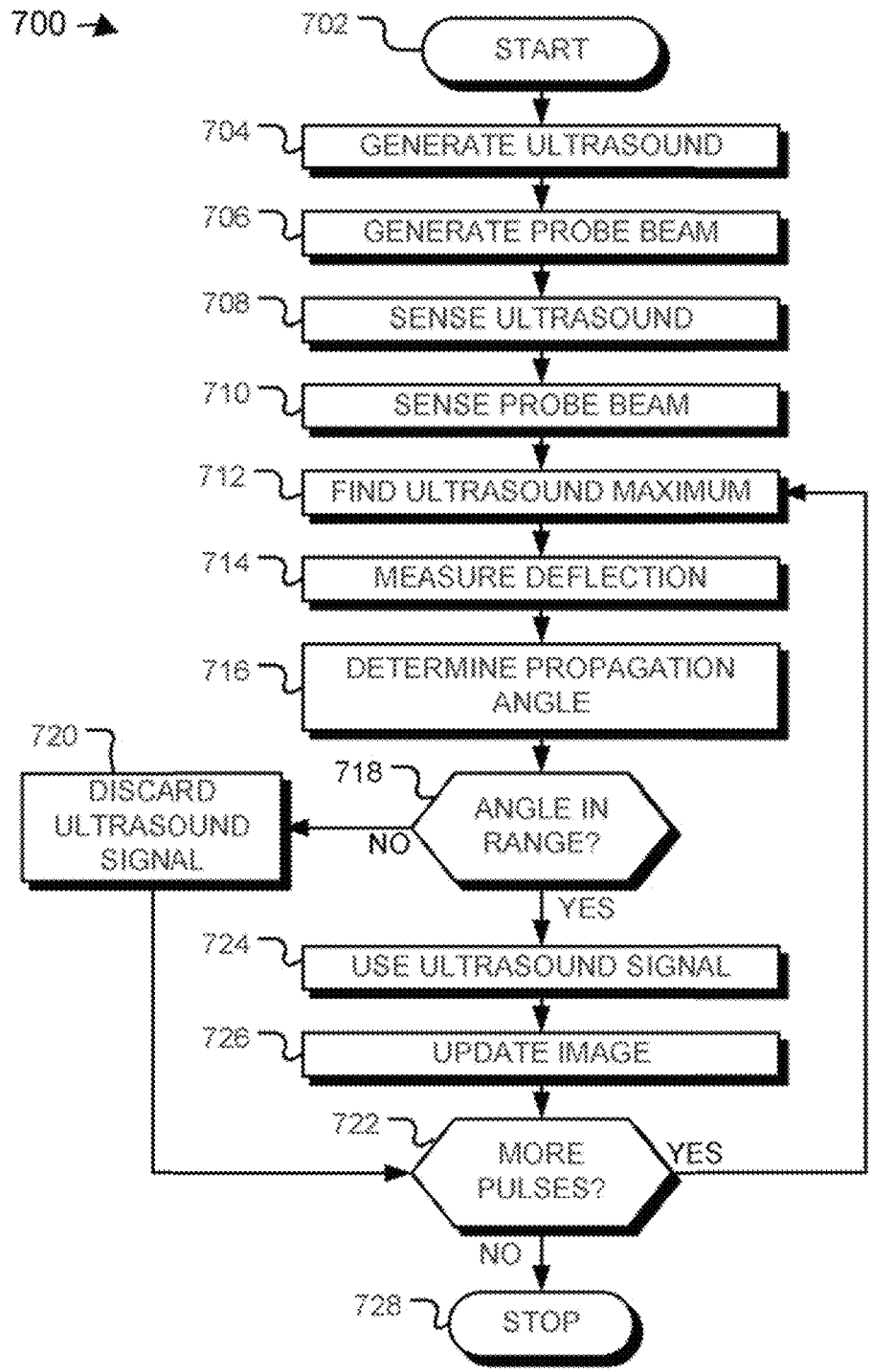
FIG. 7 is a flow chart of a method of off-axis artifact reductions, consistent with embodiments of the disclosure.

FIG. 7 is a flow chart of a method 700 for constructing an image in an ultrasound imaging system, such as the system 100 of FIG. 1. Following start block 702, an ultrasound pulse is generated in an object to be imaged (block 704). This may be done, for example, using a piezoelectric transducer or a photo-acoustic generator. A probe beam, such as a laser beam, is generated and transmitted through a coupling element containing a medium that supports the propagation of ultrasound waves and the probe beam (block 706). Ultrasound emitted from the object in response to the generated ultrasound is coupled to an ultrasound detector via the coupling element and is sensed (block 708). Deflection of the probe beam is caused by refractive index changes in the medium within the coupling element that are due to the passage of the ultrasound wave is sensed (block 710).

A maximum amplitude of a first signal from the ultrasound detector is identified (block 712). For example, in FIG. 2, the first maximum in the graph 208 occurs at time T1. In an embodiment where the deflection detector is a quadrature photodiode, the spatial components of the probe beam deflection (e.g., X and Y in equation (2)) at the time of the identified maximum are determined from the signals (a, b, c and d) from the quadrature photodiode (block 714). The probe beam deflection angle (signal of graph 210 in FIG. 2), which is indicative of the propagation angle of the second ultrasound pulse 204 is obtained from the spatial components using equation (3) above (block 716). If the determined propagation angle is outside of a specified range, as depicted by the negative branch from decision block 718, the corresponding first signal is discarded (block 720). The range may be, for example, $90°\pm\alpha$ from aperture of the ultrasound detector ($0°\pm\alpha$ from the axis of the ultrasound detector). The angle, $\alpha$, may be 1° or less, for example. In particular, the range may be less than the angular resolution of the ultrasound detector. Flow continues to decision block 722 where it is determined if any more pulses have been found in the signal of the first signal path from the ultrasound detector. If more pulses are found, the flow returns to block 712. If the determined propagation angle is within the specified range, as depicted by the positive branch from decision block 718, the corresponding first signal is saved at block 724 for use in constructing an image of the object. The image is updated using the saved signal (block 726). The image may be constructed using time-reversal back projection, for example. If no more pulses are found, as depicted by the negative branch from decision block 722, the process terminates (block 728).

Thus, in accordance with an embodiment of the disclosure, a method for imaging an object comprises coupling ultrasound from the object through a coupling element to an ultrasonic detector to provide a first signal indicative of ultrasound at the ultrasonic detector, propagating an electromagnetic probe beam through the coupling element to a probe beam deflection detector to provide a second signal indicative of an angle of propagation of the ultrasound through the coupling element, determining, from the second signal, one or more time intervals during which the angle of propagation, through the coupling element, of ultrasound received at the ultrasound detector is in a first range of angles, and forming an image of the object from the first signal received in the one or more times intervals.

When used in a scanning ultrasound imager, the image of the object may be formed from the first signal received in the one or more time intervals by determining an image pixel value from a strength of the first signal, determining a first image pixel coordinate from an arrival time of the first signal, and determining a second image pixel coordinate from a position of the ultrasound detector relative to the object.

In a further embodiment, the ultrasonic detector comprises an array of phased elements, and forming an image of the object from the first signal received in the one or more time intervals is achieved by determining an image pixel value from a strength of the first signal, determining a first image pixel coordinate from an arrival time of the first signal, and determining a second image pixel coordinate from relative phases of the array of phased elements.

Ultrasound in the object may be generated by an ultrasound source, such as piezo-electric transducer. Alternatively, ultrasound in the object may be generated by exciting the object with an electromagnetic beam to produce ultrasound in the object.

Figure 8:
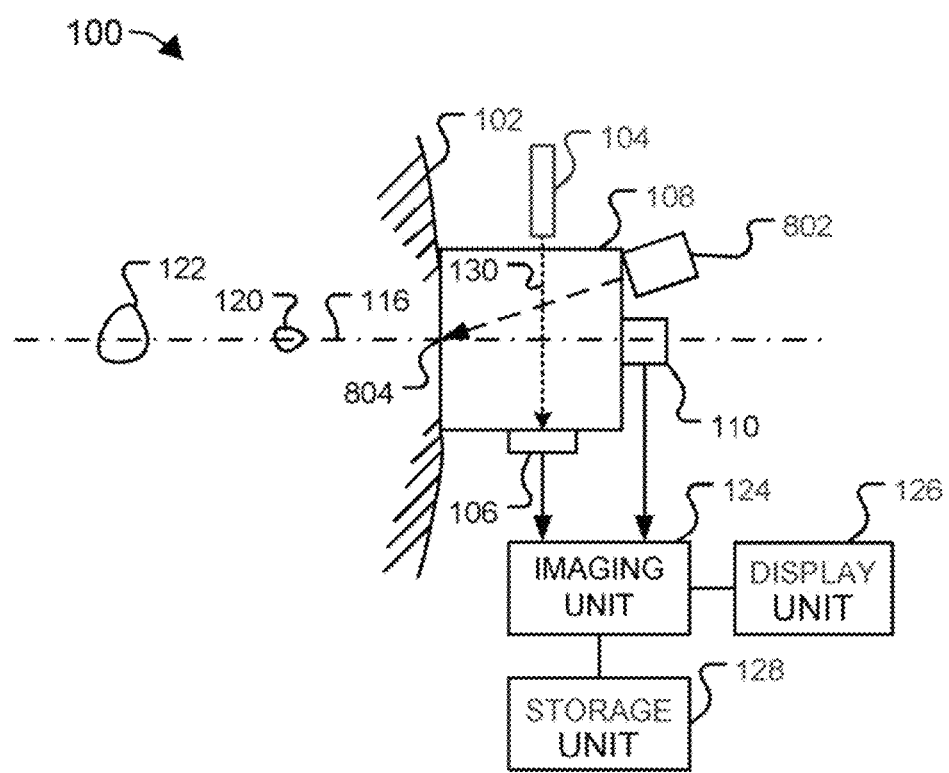
FIG. 8 is a block diagram of a further ultrasound imaging system, consistent with embodiments of the disclosure.

In a further embodiment, ultrasound in the object may be generated in response to an excitation beam generated by a second electromagnetic source and directed at the object, as shown in FIG. 8.

FIG. 8 is a further block diagram of the ultrasound imaging system 100, consistent with embodiments of the disclosure. In FIG. 8, ultrasound is generated in object 102 by action of a source 802. The source 802 may be a laser or other electromagnetic source. The source 802 directs electromagnetic energy at a region 804 on a surface of the object 102. In one embodiment, the electromagnetic energy heats the object 102 and causes a rapid local expansion in the region 804 that, in turn, generates an ultrasound wave that propagates into the object 102. In an alternative embodiment, the ultrasound detector 110 is also an ultrasound generator, such as a piezo-electric transducer.

Figure 9:
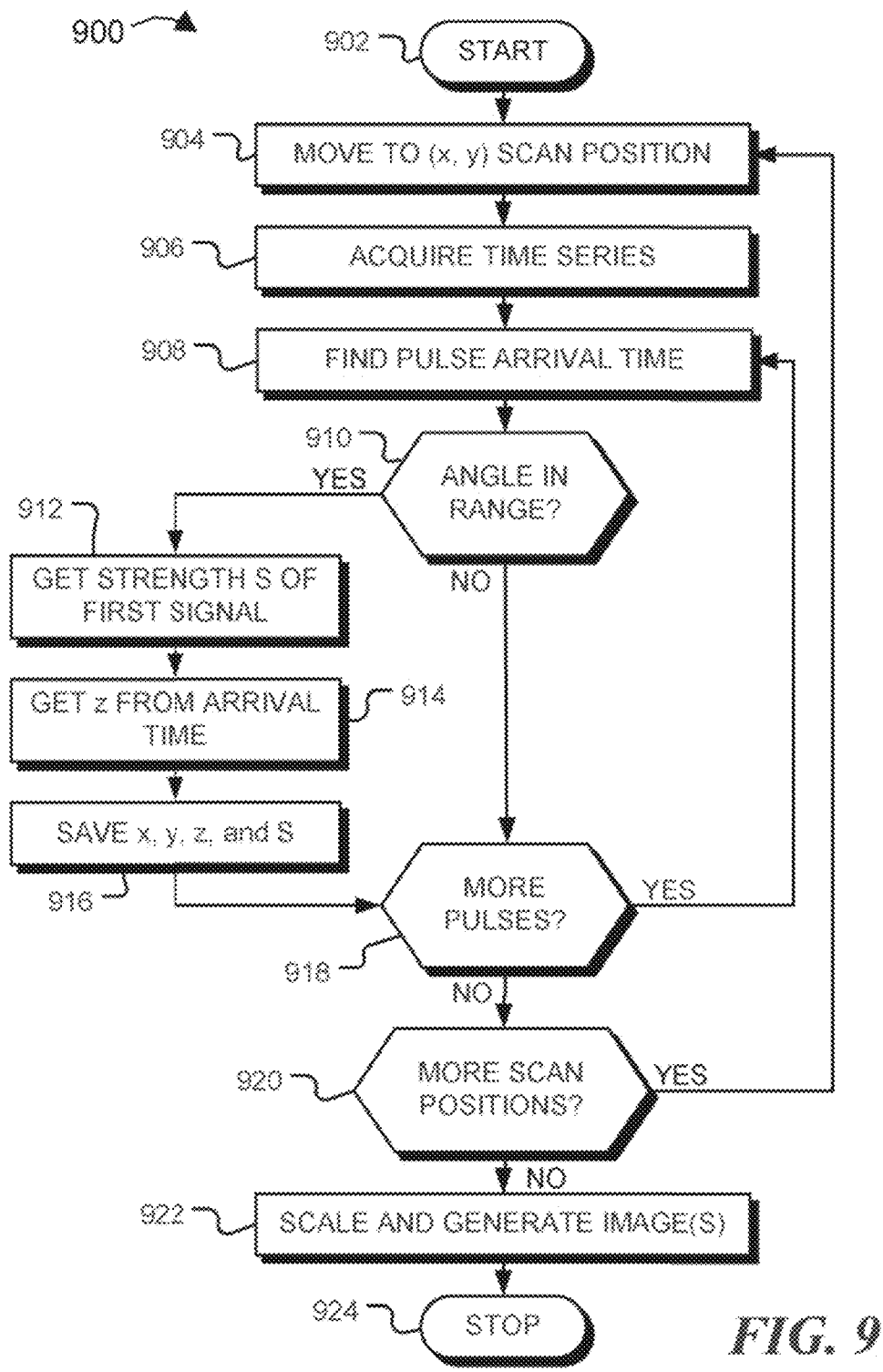
FIG. 9 is a flow chart of a method of generating a scanned image, consistent with embodiments of the disclosure.

FIG. 9 is a flow chart of a method 900 for generating an image consistent with embodiments of the disclosure. Following start block 902, an ultrasonic transducer is moved to a new scan position (block 904). Here, the position (x, y) is assumed to be in a horizontal plane, but other geometries may be used. The probe beam may be moved by an x, y scan stage for example. One or more time series are acquired from the ultrasonic transducer (such as the signal of graph 208 in FIG. 2) and the deflection sensor (such as the signals of graph 210 in FIG. 2). For example, a quadrature phase detector may provide 4 signals (one for each quadrant) or 2 difference signals (such as X and Y spatial components). The arrival time of a pulse (such as time T1 in FIG. 2) is determined by searching for a maximum in the signal associated with each pulse 202, 204, 206 (block 908). At decision block 910 it is determined, from the signal of graph 210, if the angle of incidence is close to the axis of the ultrasound transducer. This is described above with reference to FIG. 7. If the angle is within range, as depicted by the positive branch from decision block 910 the pulse is used to update the image. At block 912, the strength, S, of the ultrasound is determined from the peak, or maximum, in the signal associated with each pulse 202, 204, 206. A depth (z) of the impedance discontinuity within the object is determined from the arrival time ultrasound and the sound speed in the object. One pixel of the image is generated by assigning the value, S, to the pixel at coordinate {x, y, z} and this information is saved (block 916). Flow then continues to block 918. If the angle is not within range, as depicted by the negative branch from decision block 910, the pulse is discarded and not used for image reconstruction and flow continues to decision block 918.

At decision block 918 it is determined if there are any more pulses in the time series of the first signal. If there are more pulses, as depicted by the positive branch from decision block 918, flow returns to block 908. Otherwise, as depicted by the negative branch from decision block 918, flow continues to decision block 920. If more scan positions are required, as depicted by the positive branch from decision block 920, flow returns to block 904 and the positive of the transducer relative to the object is changed. When all scan positions have been scanned, as depicted by the negative branch from decision block 920, the pixel values may be scaled and used to generate an image at block 922. The image displays the signal values at each position in the selected frame. The image may be displayed in various forms such as a color-map, brightness map, grayscale map, contour map, or 3-dimensional surface map, for example. The method terminates at block 924. Thus, the image of the object is formed from the first signal received in the one or more time intervals during which the angle of incidence is close to the axis of the transducer. The pixel value of the image is determined from a strength S of the first signal and the image pixel z-coordinate is determined from an arrival time of the first signal and the x- and y-coordinates of the pixel are determined from the position of the ultrasound detector relative to the object.

While this invention is susceptible of being embodied in many different forms, there is shown in the drawings and is herein described in detail specific embodiments, with the understanding that the present disclosure is to be considered as an example of the principles of the invention and not intended to limit the invention to the specific embodiments shown and described. In the description above, like reference numerals may be used to describe the same, similar, or corresponding parts in the several views of the drawings.

The term "configured" or the like may relate to the capability of a device whether the device is in an operational or non-operational state. Configured may also refer to specific settings in a device that effect the operational characteristics of the device whether the device is in an operational or non-operational state. In other words, the hardware, software, firmware, registers, memory values, and/or the like may be "configured" within a device, whether the device is in an operational or nonoperational state, to provide the device with specific characteristics. Terms such as "a control message to cause in a device" may mean that a control message has parameters that may be used to configure specific characteristics in the device, whether the device is in an operational or non-operational state.

In addition, it should be understood that any figures that highlight any functionality and/or advantages, are presented for example purposes only. The disclosed architecture is sufficiently flexible and configurable, such that it may be utilized in ways other than that shown. For example, the steps listed in any flowchart may be re-ordered or only optionally used in some embodiments.

While various embodiments have been described above, it should be understood that they have been presented by way of example, and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments. Thus, the present embodiments should not be limited by any of the above-described exemplary embodiments.

The method steps of the implementations described herein are intended to include any suitable method of causing such method steps to be performed, consistent with the patentability of the following claims, unless a different meaning is expressly provided or otherwise clear from the context.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the scope of this disclosure and are intended to form a part of the disclosure as defined by the following claims, which are to be interpreted in the broadest sense allowable by law.

The invention claimed is:

1. A method for imaging an object comprising:
   transmitting an ultrasound pulse toward the object so that the object reflects an acoustic signal;
   receiving the acoustic signal at an ultrasound detector, the ultrasound detector and the object forming a transducer axis therebetween, wherein a coupling element is positioned between the object and the ultrasound detector;
   generating and directing a probe beam toward the acoustic signal, the probe beam in a direction orthogonal to the transducer axis;
   receiving a deflected probe signal at a probe beam deflection detector resulting from an interaction between the probe beam and the acoustic signal, wherein the coupling element is positioned between the object and the probe beam deflection detector;
   determining, with Snell's law and from the deflected probe signal, an angle of incidence between the transducer axis and a direction of propagation of the acoustic signal;
   providing a filtered acoustic signal by removing portions of the acoustic signal at time intervals during which the determined angle of incidence is greater than a threshold range of angles; and
   forming an image of the object from the filtered acoustic signal.

2. The method of claim 1, wherein forming the image of the object further comprises:
   determining an image pixel value from a strength of the received acoustic signal;
   determining a first image pixel coordinate from an arrival time of the received acoustic signal; and
   determining a second image pixel coordinate from a position of the received acoustic wave at the ultrasound detector.

3. The method of claim 1, further comprising:
   determining, from the received acoustic signal and the deflected probe signals, one or more time intervals during which an angle of propagation of the acoustic signal is within a range of propagation angles;
   detecting a first time at which an amplitude of the received acoustic signal is at a maximum;

determining a probe beam deflection angle associated with the deflected probe signal at the first time; and determining the angle of propagation of the acoustic wave from an amplitude of the deflected probe signal at the first time.

4. The method of claim 1, wherein the threshold range of angles coincides with an angular resolution of an ultrasonic detector.

5. The method of claim 1, wherein the probe beam deflection detector is a quadrature photodiode.

6. The method of claim 2, wherein forming the image of the object further comprises:

constructing the image using a time-reversal, back-propagation technique.

* * * * *